US011060995B1

(12) United States Patent
Botte et al.

(10) Patent No.: US 11,060,995 B1
(45) Date of Patent: Jul. 13, 2021

(54) RAPID VIRAL DIAGNOSTIC SENSOR (71) Applicant: Texas Tech University System, Lubbock, TX (US)

(72) Inventors: Gerardine G. Botte, Lubbock, TX (US); Ashwin Ramanujam, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 16/933,686

(22) Filed: Jul. 20, 2020

(51) Int. Cl.
G01N 27/327 (2006.01)
C12N 7/00 (2006.01)
A61B 5/145 (2006.01)

(52) U.S. Cl.
CPC ..... *G01N 27/3271* (2013.01); *A61B 5/14532* (2013.01); *A61B 5/14546* (2013.01); *C12N 7/00* (2013.01); *G01N 27/3275* (2013.01); *G01N 2333/01* (2013.01)

(58) Field of Classification Search
CPC .... G01N 27/327–3272; G01N 27/3275–3278; G01N 2333/005–19
See application file for complete search history.

(56) References Cited

U.S. PATENT DOCUMENTS 5,509,410 A * 4/1996 Hill ............... A61B 5/1486
204/403.04
5,653,864 A * 8/1997 Gotoh ............... G01N 27/3273
204/403.09
2002/0123048 A1 * 9/2002 Gau ............... B82Y 30/00
435/6.11
2014/0014534 A1 * 1/2014 Surareungchai ....... G01N 33/02
205/780.5

OTHER PUBLICATIONS

Cheng et al. "Fabrication of NiOOH/Ni(OH)2@C Electrode for Detecting Blood Glucose by Composited Plating Method," Int. J. Electrochem. Sci., 11 (2016) 6085-6094 (Year: 2016).*
01 Nickel properties on the Nickel Institute website downloaded Sep. 10, 2020 fromhttps://nickelinstitute.org/about-nickel#01-nickel-properties (Year: 2020).*
Gupta et al., "Correlation of salivary glucose level with blood glucose level in diabetes mellitus," J Oral Maxillofac Pathol. Sep.-Dec. 2017 21(3): 334-339 (Year: 2017).*

(Continued)

*Primary Examiner* — Alexander S Noguerola
(74) *Attorney, Agent, or Firm* — Dickinson Wright PLLC; Kristopher Lance Anderson (57) ABSTRACT

The present invention provides for a device and method for the rapid detection (within seconds) of viruses and virions (proteins and nucleic acids) found in novel coronavirus (SARS-CoV-2), Human Immunodeficiency Virus (HIV), and other pandemic viruses. The device can be used at front line, hospitals, clinical laboratories, airports, groceries, homes, and the like. The device can be used as a single probe for single use or home use, or the device integrated into a carrousel or multiple probe magazine for fast detection of multiple samples simultaneously. This carrousel would facilitate multiple testing at times of pandemics when a large number of samples have to be tested in short periods of time.

27 Claims, 7 Drawing Sheets (56) References Cited

OTHER PUBLICATIONS

Nakamura et al., "Diurnal Changes in Salivary Amino Acid Concentrations," in vivo 24: 837-842 (2010) (Year: 2010).*
Leal et al., "Physiochemical properties of mucus and their impact on transmucosal drug delivery," International Journal of Pharmaceutics 532 (2017) 555-572 (Year: 2017).*
Huang et al., "Structural and functional properties of SARS-CoV-2 spike protein: potential antivirus drug development for COVID-19," Acta Pharmacolgica Sinica (2020) 41:1131-1149 (Year: 2020).*
Grant et al., Analysis of the SARS-CoV-2 spike protein glycan shield reveals implications for immune recognition, Scientific Reports (2020) 10:14991 (Year: 2020).*
Cheng et al. "Fabrication of NiOOH/Ni(OH)2@C Electrode for Detecting Blood Glucose by Composited Plating Method," International Journal of Electrochemical Science, 11 (2016) 6085-6094 (Year: 2016), 10 pages.
01 Nickel properties on the Nickel Institute website downloaded Sep. 10, 2020 from https://nickelinstitute.org/about-nickel#01-nickel-properties (Year: 2020), 10 pages.
Gupta et al., "Correlation of salivary glucose level with blood glucose level in diabetes mellitus," Journal of Oral Maxillofacial Pathology Sep.-Dec. 2017; 21(3): 334-339 (Year: 2017), 16 pages.
Nakamura et al., "Diurnal Changes in Salivary Amino Acid Concentrations," in vivo 24: 837-842 (2010) (Year: 2010), 6 pages.
Leal et al., "Physiochemical properties of mucus and their impact on transmucosal drug delivery," International Journal of Pharmaceutics 532 (2017) 555-572 (Year: 2017), 18 pages.
Xu et el. Beware of the second wave of COVID-19. The Lancet vol. 395, 1321-1322 (2020), 3 pages.
D'Arienzo et al. "Assessment of the SARS-CoV-2 basic reproduction number, R0, based on the early phase of COVID-19 outbreak in Italy" Biosafety and Health 2 (2020) 57-59, 3 pages.
Li et al. "Early Transmission Dynamics in Wuhan, China, of Novel Coronavirus—Infected Pneumonia" The New England Journal of Medicine 382, 1199-1207 (2020), 10 pages.
Li et al. "Substantial undocumented infection facilitates the rapid dissemination of novel coronavirus (SARS-CoV-2)" Science 368, 489-493 (2020), 6 pages.
Wang et al. "Clinical Characteristics of 138 Hospitalized Patients With 2019 Novel Coronavirus-Infected Pneumonia in Wuhan, China" JAMA 323, 1061 (2020), 9 pages.
Tang et al. "Laboratory Diagnosis of COVID-19: Current Issues and Challenges" Journal of Clinical Microbiology vol. 58, Issue 6 e00512-20 (2020), 9 pages.
Dheda et al. "Diagnosis of COVID-19: Considerations, Controversies and Challenges in South Africa" Wits Journal of Clinical Medicine 2, 3 (2020), 8 pages.
Yang et al. "PCR-based diagnostics for infectious diseases: uses, limitations, and future applications in acute-care settings." The Lancet Infectious Diseases 4, 337-348 (2004), 12 pages.
Gutierres et al. "Point-of-Care Testing: An Introduction" The Annals of Pharmacotherapy 38, 119-125 (2004), 7 pages.
Gandhi et al. "Asymptomatic Transmission, the Achilles' Heel of Current Strategies to Control Covid-19" The New England Journal of Medicine 382, 2158-2160 (2020), 4 pages.
Wang et al. "Detection of SARS-CoV-2 in Different Types of Clinical Specimens" JAMA vol. 323, No. 18 (2020), 2 pages.
Zou et al. "SARS-CoV-2 Viral Load in Upper Respiratory Specimens of Infected Patients" The New England Journal of Medicine 382, 1177-1179 (2020), 4 pages.
Kim et al. "Comparison of Nasopharyngeal and Oropharyngeal Swabs for the Diagnosis of Eight Respiratory Viruses by Real-Time Reverse Transcription-PCR Assays" PLoS ONE vol. 6, Issue 6 (2011), 7 pages.
Blaschke et al. "Non-invasive sample collection for respiratory virus testing by multiplex PCR" Journal of Clinical Virology 52, 210-214 (2011), 5 pages.
Bilder et al. "Salivary Detection of H1N1 Virus: A Clinical Feasibility Investigation" J Dent Res 90, 1136-1139 (2011), 4 pages.
Sindhu et al. "Saliva: A Cutting Edge in Diagnostic Procedures" Journal of Oral Diseases 2014, 1-8 (2014), 9 pages.
Azzi et al. "Saliva is a reliable tool to detect SARS-CoV-2" Journal of Infection 81, e45-e50 (2020), 6 pages.
To et al. "Consistent Detection of 2019 Novel Coronavirus in Saliva" Clinical Infectious Diseases vol. 71 (2020), 3 pages.
Williams et al. "Saliva as a non-invasive specimen for detection of SARS-CoV-2" Journal of Clinical Microbiology (2020) doi:10.1128/JCM.00776-20, 5 pages.
Vedharathinam et al. "Understanding the electro-catalytic oxidation mechanism of urea on nickel electrodes in alkaline medium" Electrochimica Acta 81, 292-300 (2012), 9 pages.
Seo et al. "Rapid Detection of COVID-19 Causative Virus (SARS-CoV-2) in Human Nasopharyngeal Swab Specimens Using Field-Effect Transistor-Based Biosensor" ACS Nano 14, 5135-5142 (2020), 8 pages.
Thevenot et al. "Electrochemical Biosensors: Recommended Definitions and Classification*" Analytical Letters 34, 635-659 (2001), 28 pages.
Klinger et al. "Cloaked similarity between HIV-1 and SARS-CoV suggests an anti-SARS strategy" BMC Microbiology 7 (2003), 7 pages.
Khodamoradi et al. "Co-infection of Coronavirus Disease 2019 and Influenza A: A Report from Iran" Arch Iran Med 23, 239-243 (2020), 6 pages.
Kim et al. "Rates of Co-infection Between SARS-CoV-2 and Other Respiratory Pathogens" JAMA 323, 2085 (2020), 2 pages.
Konala et al. "Co-infection with Influenza A and COVID-19" European Journal of Case Reports in Internal Medicine 7, 1 (2020), 4 pages.
Aydin et al. "HIV/SARS-CoV-2 coinfected patients in Istanbul, Turkey" Journal of Medical Virology (2020) doi:10.1002/IMV. 25955, 4 pages.
Zhu et al. "Co-infection of SARS-CoV-2 and HIV in a patient in Wuhan city, China" Journal of Medical Virology 92, 529-530 (2020), 3 pages.
Parker et al. "HIV and SARS-CoV-2 co-infection: The diagnostic challenges of dual pandemics" S Afr Med J 110, (2020), 3 pages.
Wang et al. "Detection of SARS-associated Coronavirus in Throat Wash and Saliva in Early Diagnosis" Emerging Infectious Diseases 10, 1213-1219 (2004), 8 pages.
Liu et al. "Epithelial Cells Lining Salivary Gland Ducts Are Early Target Cells of Severe Acute Respiratory Syndrome Coronavirus Infection in the Upper Respiratory Tracts of Rhesus Macaques" Journal of Virology 85, 4025-4030 (2011), 6 pages.
Xu et al. "Salivary Glands: Potential Reservoirs for COVID-19 Asymptomatic Infection" Journal of Dental Research 002203452091851 (2020) doi:101177/0022034520918518, 1 page.
Sabino-Silva et al. "Coronavirus COVID-19 impacts to dentistry and potential salivary diagnosis" Clinical Oral Investigations 24, 1619-1621 (2020), 3 pages.
Humphrey et al. "A review of saliva: Normal composition, flow, and function" The Journal of Prosthetic Dentistry 85, 162-169 (2001), 8 pages.
Lopin et al. "PSoC-Stat: A single chip open source potentiostat based on a Programmable System on a Chip" PLoS ONE 13, e0201353 (2018), 22 pages.
Ramanujam et al. "Online Sensor Device for Rapid *Escherichia coli* Detection in Water" In ECS Meeting Abstracts; 2018, 1 page.
Jiang "COVID-19 Diagnostics: Technologies, Players and Trends" IDTechEx. (accessed Jun 19, 2020), 3 pages.
Pasomsub et al. "Saliva sample as a non-invasive specimen for the diagnosis of coronavirus disease 2019: a cross-sectional study" Clinical Microbiology and Infection (2020) doi:10.1016/tcmi.2020.05.001, 4 pages.

* cited by examiner

Single Probe

FIG. 1

Multiprobe Carousel

RAPID VIRAL DIAGNOSTIC SENSOR

CROSS-REFERENCE TO RELATED APPLICATIONS

None.

TECHNICAL FIELD

The present invention relates in general to the field of pathogen detection technologies. In particular, the system provides for rapid detection of desired viruses and virions. The device and method for rapid detection of viruses and virions in accordance with the present invention results in rapid detection of them at the point of care, often within seconds. The disclosed systems and methods support detection in the novel coronavirus (SARS-CoV-2) and related products and services.

STATEMENT OF FEDERALLY FUNDED RESEARCH

None.

BACKGROUND OF THE INVENTION

With the total number of confirmed cases related to SARS-CoV-2 crossing the 4 million mark, along with the death of over 298,000 infected individuals (as per the Coronavirus Resource Center of Johns Hopkins University), it is critical to ensure early detection of individuals affected by this virus. Apart from this deadly corona virus, viruses such as Human Immunodeficiency Virus (HIV) have long been the reason for causing another deadly disease in AIDS. About 1.1 million people were infected by HIV in the US by the end of 2016 and over 37,000 received HIV diagnosis only in 2018 in the US (according to statistics from CDC). Hence, early detection is of vital importance in nursing these patients at the earliest possible. Techniques like the quantitative reverse transcriptase polymerase chain reaction (qRT-PCR) require hours before they can confirm the presence or absence of the virus in a sample. Moreover, with the cases increasing exponentially, it can only be foreseen that there would be a lot more samples to be tested and this could potentially cause a delay in valuable time. The requirement for point-of-care detection devices are of high significance now more than ever. Such devices can be deployed anywhere starting from hospitals, clinical laboratories to airports, grocery stores and other places where there are people still gathering for basic needs. Apart from these places, if such devices are feasible to be manufactured in bulk, they can be used by the people staying at home in isolation to check themselves for exposure to the virus by following a standard operating procedure.

SUMMARY OF THE INVENTION

The present invention therefore enables the rapid detection (within seconds) of viruses and virions (proteins and nucleic acids) found in novel coronavirus (SARS-CoV-2), Human Immunodeficiency Virus (HIV), and other pandemic viruses. The device can be used at front line, hospitals, point-of-care, clinical laboratories, airports, groceries, homes, and the like. The device can be used as a single probe or integrated into a carrousel for fast detection of multiple samples simultaneously. This carrousel would facilitate multiple testing at times of pandemics when a large number of samples have to be tested.

The present invention provides a portable sensor, called "RAnCODS-19". RAnCODS-19 is a portable sensor for COVID-19 diagnostics that would enable continuous monitoring for quantification of the virus all the way from saliva to blood plasma samples. The proof of concept has been demonstrated in saliva samples and available for testing clinical samples. The RAnCODS-19 test may further be a multi-probe device is expected to test 2400 samples per hour, which is more than a 100-fold increase compared to most other techniques being used currently. Once scaled up for manufacturing, each single probe and multiprobe device should be able to test and return results for thousands of samples a day at hospitals, clinical laboratories, airports, schools, universities, workplaces, and our homes.

RAnCODS-19 is a standalone electrochemical sensor device with the ability to quantitatively detect the novel corona virus (SARS-CoV-2) in saliva samples within 100 milliseconds. This prototype has been validated to detect the presence of spike protein S1 of SARS-CoV-2 mixed in artificial saliva. In one aspect the RAnCODS-19 sensor is able to indicate presence and absence of the viral protein and measure in range of 0 to 2.5 µg/mL of the spike protein. The sensitivity of the sensor is 0.25 $(mA/cm^2)/(µg/mL)$ while its limit of detection is 0.04 µg/mL.

With the rapid detection of SARS-CoV-2 as provided by the present invention, diagnostics teams can extensively test clinical samples using point-of-care single probe and multiprobe carousel approaches to expedite the testing procedure. It is a critical aspect of the present invention that is uses a non-invasive sampling of saliva. The sensor is portable and envisioned to be integrated with its own electronics, and encrypted data storage components to store the results on cloud and made available via a mobile device application with dual-authentication sign-in to protect patient confidentiality.

Apart from saliva samples, the sensor works in blood plasma to accelerate the screening of samples to be tested further by standard techniques, if needed. This is another potential route for prioritizing the samples based on the level of infection.

In general, in one embodiment, the invention features a sensor for detecting a virus with a sensor tip. The sensor tip includes a working electrode that includes a conductive material that is resistant to corrosion, a support, and a catalyst. The sensor tip also includes a counter electrode with an electrocatalyst. The counter electrode is operably connected to the working electrode. The sensor tip allows for the change in current to be detected when the sensor tip is inserted into a media, through the use of the working electrode and the counter electrode. By detecting the change in current, the sensor tip is able to detect the virus.

Implementations of the invention can include one or more of the following features:

The sensor can include a reference electrode that includes a reference material.

The reference material can be selected from a group consisting of Pt, Au, Ag, Ti, Rh, Ru, and combinations thereof.

The sensor tip when inserted into the media can detect change in current utilizing the reference material in combination with the working electrode and the counter electrode.

The support can be selected from a group consisting of Nickel, Nickel gauze, Nickel mesh, Ti, stainless steel, Hastelloy, graphite, nickel foam, Ti foam, Aluminum, Aluminum foam, carbon, carbon fibers, and graphene.

The catalyst can include a transition metal.

The transition metal can be selected from a group consisting of Ni, Fe, Co, Cr, Mo, Rh, Ru, Pd, Ir, Au, Pt, composites of graphene metal, and combinations thereof.

The transition metal can include Ni.

The support can include the catalyst.

The electrocatalyst can be selected from a group consisting of Pt, Au, Ir, Ni, Ti, Rh, Ru, and combinations thereof.

The virus being detected can be selected from a group consisting of coronavirus (SARS-CoV-2), Human Immunodeficiency Virus (HIV), pandemic viruses, and combinations thereof.

The sensor can detect the virus within a time period in the range between 10 milliseconds and 10 seconds.

In another aspect, the sensor can detect the virus within 100 milliseconds.

The sensor can detect concentration of the virus in a sample.

The sensor can detect concentration of a second virus in the sample.

In general, in another embodiment, the invention features a method for detecting a virus with a sensor tip. The method includes selecting a sensor tip, which has a working electrode including a conductive material, a counter electrode including an electrocatalyst, and a reference electrode that can be connected to the counter electrode and the reference electrode. The method further includes creating a catalyst locally on the sensor tip at a particular voltage corresponding to the working electrode and the reference electrode. The method further includes inserting the sensor tip into a media. The method further includes rotating the sensor tip at a particular rotation speed. The method further includes applying a cell voltage between the working electrode and the reference electrode. The method further includes holding the sensor tip at a particular temperature. The method further includes calibrating a change in current between a media blank, which does not contain the virus, and the media. In this method, the change in current is calibrated as a function of concentration of the virus present in the media.

Implementations of the invention can include one or more of the following features:

The virus being detected can be selected from a group consisting of coronavirus
(SARS-CoV-2), Human Immunodeficiency Virus (HIV), pandemic viruses, and combinations thereof.

The sensor can detect the virus within a time period in the range between 10 milliseconds and 10 seconds.

In another aspect, the sensor can detect the virus within 100 milliseconds.

The media that the sensor tip is inserted into can include a single sample.

The single sample can enable calibrating a single probe.

The media that the sensor is inserted into can include multiple samples.

The multiple samples can enable calibrating multiple probes simultaneously.

The media can include a composition, a sample, and pH adjusting salts.

The composition can transport the sample across the media.

The sample can be selected from a group consisting of Saliva, Mucus, Plasma, Phosphate buffered saline (PBS), Dulbecco's Phosphate buffered saline (DPBS), and combinations thereof.

The pH adjusting salts can be selected from a group consisting of KOH, NaOH, ammonium solutions, phosphate buffers, and combinations thereof.

The particular rotation speed can be in a range between 0 rpm and 3000 rpm.

The cell voltage can be in a range between −0.5 V and 1.0 V relative to voltage of the reference electrode.

The particular temperature can be in a range between 10° C. and 40° C.

The sensor can detect concentration of a second virus in the sample.

BRIEF DESCRIPTION OF THE DRAWINGS

For a detailed description of example embodiments, reference will now be made to the accompanying drawings in which.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

Figure 1:
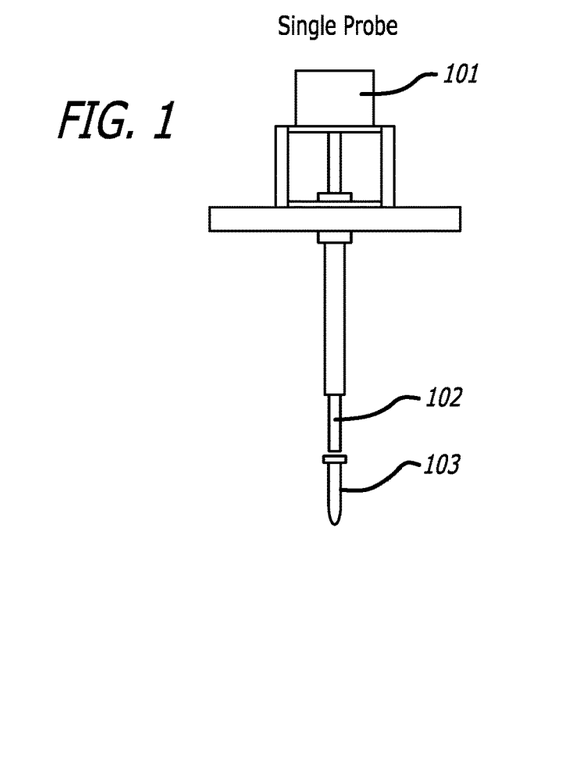
FIG. 1 depicts a schematic diagram of the device—a single probe—as implemented as the RAnCODS-19 sensor.
Figure 3A:
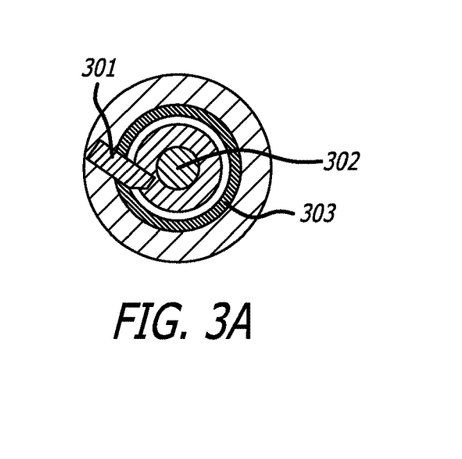
FIG. 3A depicts a sensor probe containing the working electrode (e.g., nickel disk substrate) at the center surrounded by a concentric counter electrode (e.g., Pt ring) and a small quasi reference electrode (e.g., Pt foil).

In one embodiment, the present invention comprises an amperometric sensor, termed the RAnCODS-19 sensor, that utilizes the constant potential oxidation of nickel hydroxide (Ni(OH)2) (or other potential transition metals, such as Co, Cr, Rh, Ir, Au, Pt, etc.) to nickel oxyhydroxide (NiOOH) (or equivalent) on a rotating disk electrode (RDE) in alkaline media (alkaline enough to increase the sensitivity of the sensor while maintaining the virions and viruses viable for quantification). The RDE technique is applied using a small size electrode (e.g., 1-5 mm diameter or microelectrodes<0.5 μm) to introduce controlled, consistent mass transport of hydroxyl ions, viruses, and/or virions to the surface of the electrocatalyst electrode and to provide a uniform current distribution on the electrode. FIG. 3A shows the configuration of the RAnCODS-19 sensor including working electrode (WE) 302, reference electrode (RE) 301, and counter electrode (CE) 303. In the example, nickel (Ni) is used as working electrode 302, while Platinum (Pt) is used as the quasi-reference electrode 301 and counter electrodes 303 (due to its stability in the media), respectively.

Transition metals such as nickel, are converted into an electrocatalyst in-situ according to reaction (1) by applied a control potential:

$$Ni(OH)_2+OH^- \rightleftharpoons NiOOH+H_2O+e^- \quad (1)$$

RAnCODS-19 is an electrochemical sensor with a nickel working electrode. When nickel is placed in an alkaline medium, it is chemically oxidized to nickel hydroxide. This nickel hydroxide upon electrochemical oxidation forms nickel oxyhydroxide as shown in reaction (1). In the presence of SARS-CoV-2 spike protein (found on outer surface of virions), modifications to the electrochemical oxidation reaction occur due to a competing reaction between the viral protein and hydroxyl ions at the electrode/electrolyte interface. This leads to a current response that is distinct from the current response obtained in the absence of the protein. This current distinction indicates if the viral protein is present in a sample or not.

Viruses and virions interact with the electrode surface 307, such as an RDE Substrate/Support providing a nickel oxyhydroxide (NiOOH) electrocatalyst (or transition metal oxyhydroxide) 306, as shown in FIG. 3B, as a result, the current is altered in contacting the bulk media 304 when compared to blank media, indicating the presence of viruses, depending on the fluid, stream, composition, etc. The change in the current is associated with the concentration of the viruses 305, such as SARS-CoV-2 or HIV In the methodology, the media 304 is controlled such that the current response is associated with the "species of interest" to be detected. That is a key aspect of the methodology or standard operating procedure for the sensor of the present invention.

A critical advantage of the RAnCODS-19 sensor (over electrochemical biosensors) lies in the fact that the nickel oxyhydroxide (NiOOH) electrocatalyst (or transition metal oxyhydroxide) 306 can be generated locally (in-situ) at the electrode surface as and when required. Hence, it eliminates the complications in design of enzymatic biosensors where there is always a potential threat that the inactivation of enzymes could hinder the sensing process. The catalyst is regenerated as needed enabling the reuse of the probe. In addition, the regeneration of the catalyst involves a strong alkaline (e.g., pH>14) environment which acts as a disinfection mechanism for the probe components, eliminating costs of probes disposal as in typical electrochemical biosensors.

The applied potential during the measurement can be calibrated for different viruses and virions (either proteins or nucleic acids) present in different types of viruses, enabling multiple detection of viruses and their discrimination in a single sample. In summary the technology enables: (1) fast detection of viruses, (2) resilient and reusable sensor tip, (3) discrimination of viruses in a single sample, (4) single and multiple measurements simultaneously.

The current state of art techniques for COVID-19 diagnosis include qRT-PCR based devices, lateral flow assays, point of care molecular diagnosis devices and their hybrid systems. Table 1 presents a comparison of the advantages of the RAnCODS-19 sensor when compared to current methods. For, HIV the state of art diagnostic techniques include laboratory testing such as enzyme linked immunosorbent assays followed by Western blot analysis to ensure their successful detection.

TABLE 1

Comparison of RAnCODS-19 on various key parameters with currently available technologies for COVID-19 diagnostics.

| | qRT-PCR (device) | POC MDx (device) | LFAs (Device) | Hybrid Systems | RAnCODS-19 (present invention) |
|---|---|---|---|---|---|
| Limit of detection (copies/ml) | 100-1000 | 125-500 | N/A | 10-10000 | 0.04 μg/ml |
| Test time | >2 hours | 5-45 mins | 10-30 mins | 30-90 mins | <100 ms |
| Sample-answer time | ~4 to 6 days | ~1 hour | ~30 mins | >1 hour | ~2 mins (single probe) 15-30 s (multiprobe carousel) |
| Price (per test) | <$5 | $10 to $150 | $0.5 to $5 | Depends on technology | <$0.5 (cost of solutions) |
| Price (per platform) | $15k to $90k | $5k to $10k | <$1k | $500 to $5k | ~<$250 (single probe device)* ~<1.5k (multiprobe device)* |
| Sample Collection | Nasal Swab | Sputum | Finger Prick | Finger Prick | Saliva and blood plasma samples | qRT-PCR: quantitative reverse transcriptase polymerase chain reaction, POC MDx: point-of-care molecular diagnostics, LFA: lateral flow assay.
*Assumes scale to manufacturing.

Prior references report an electrochemical microbial sensor for microbes present in water and food pathogens. However, it was not disclosed the application for viruses and virus particles such as virions or viral proteins of COVID-19, HIV, etc.

FIG. 1 shows a probe sensor operable to use with a method, in accordance with at least some embodiments. In some embodiments, the method includes selecting the probe sensor of FIG. 1, with the probe sensor having a sensor tip. In this embodiment, the sensor tip includes test electrodes. From this, the test electrodes can include a working electrode made at least partly of a conductive material, a counter electrode with an electrocatalyst, and a reference electrode. In some embodiments, the working electrode is operably connected to the counter electrode and the reference electrode. Further, the method followed in conjunction with the use of the probe sensor in FIG. 1 includes creating a catalyst locally on the sensor tip. This catalyst can be created at a particular voltage corresponding to the test electrodes. As shown in FIG. 1, the tip of the probe sensor can be inserted into the sample tube, with the sample tube containing a media. This media can include a composition, a biological sample, and pH adjusting salts. In some embodiments, the electric motor in FIG. 1 can be used to rotate the probe sensor tip at a particular rotation speed. By holding the probe sensor at a specific temperature and applying a cell voltage, in some embodiments, a change in current between a blank media sample, which does not contain any viruses or virions, and the sample tube can be calibrated as a function of the virus present in the sample tube.

The disclosed system and method herein provide sufficient diagnostics while utilizing cheaper and portable components. Accordingly, a system and method are disclosed for analyzing presence of a virus in a sample.

The single probe approach of the present invention is intended to expedite the testing procedure while the multi-probe carousel approach provides for testing of mass samples as anticipated in the field. The single probe is an embodiment capable of testing the SARS-CoV-2 samples for individual use (e.g., home-based test kits). The single probe sensor consists of an electrode 102 setup attached with a motor 101, such as an electric to rotate the electrode as seen in FIG. 1. This device is further capable of having the electric circuits and data storage components integrated to it. The probe sensor detects SARS-CoV-2 by passing a specific voltage to the electrodes 102, which are deployed into a sample tube 103 and obtaining a current response in return. The current response obtained is a result of an interaction between the electrochemical reaction occurring at the electrode 102 surface and the SARS-COV-2 present in the sample 103. Based on the concentration of SARS-CoV-2 protein in sample 103, the current response is modified.

Figure 2A:
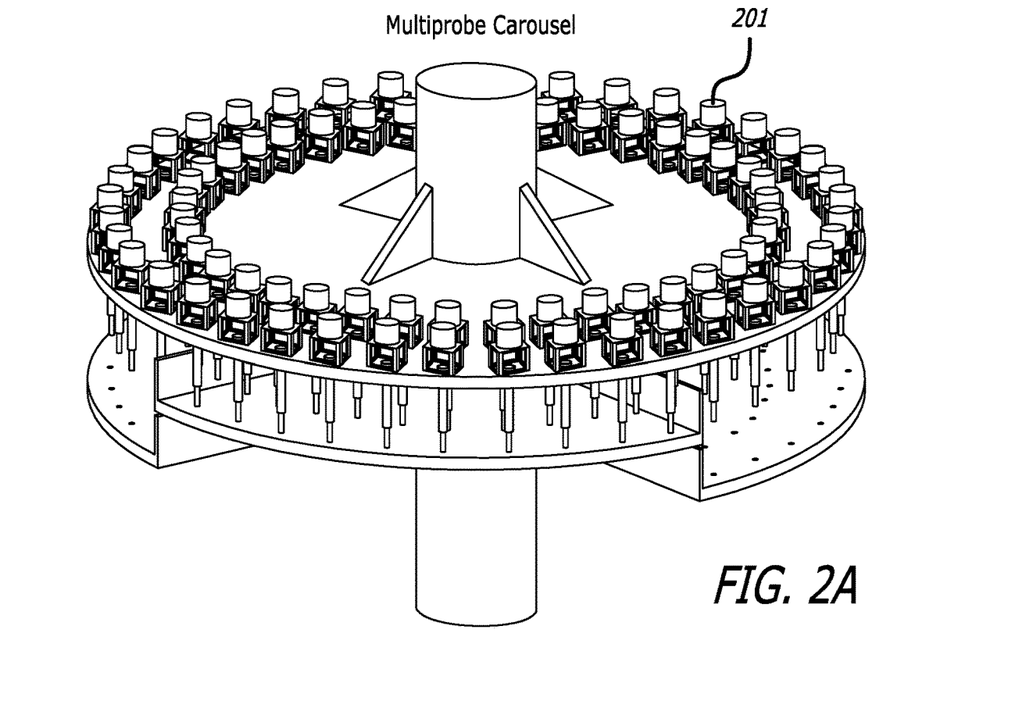
FIG. 2A depicts an example multi-probe carousel apparatus, in accordance with at least some embodiment.
Figure 2B:
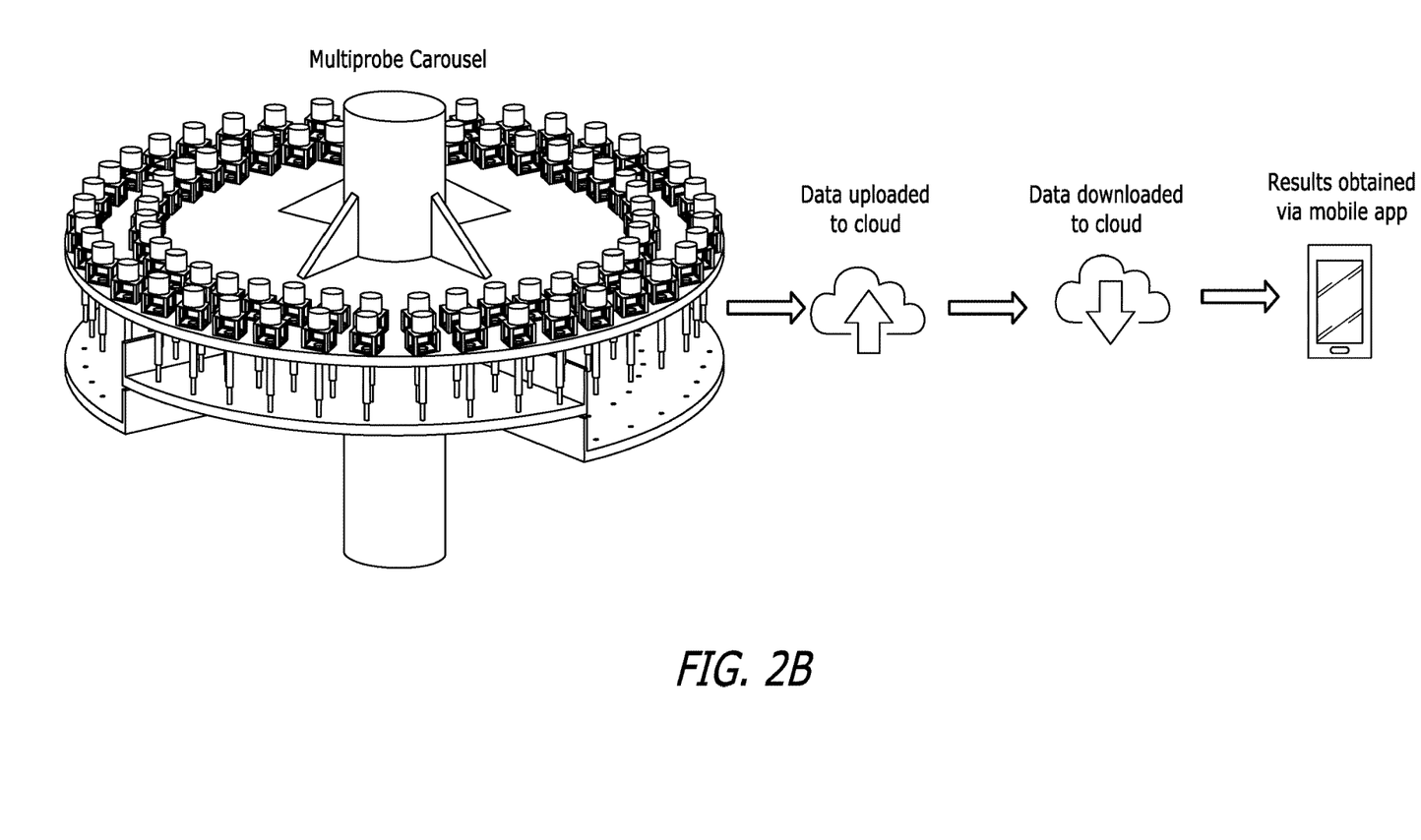
FIG. 2B depicts an exemplary multi-probe apparatus networked to a computer or mobile device for processing, in accordance with at least some embodiments.

FIG. 2A presents a schematic of the multi-probe carousel model (approximately the size of a microwave oven), having multiple numbers of individual probes 201 for testing multiple samples, for example 40 samples, every minute at pandemic frontlines and accessing the results via a mobile app by transferring the results to an encrypted cloud-based storage unit (see FIG. 2B). The multi-probe carousel is configured like a centrifuge where multiple samples can be tested simultaneously. In one exemplary embodiment the carousel depicted can hold up to 80 sensing tips of which 20 tips will be ready for testing 20 samples in a single instance. Once these 20 tips have completed testing, the next set of 20 tips will be used for testing. In the meanwhile, the 20 tips that were used for testing previously will be moved to the sterilization section, where these tips will be subject to disinfection prior to being conditioned. Once the disinfection of tips is completed, they will be conditioned/activated to form the catalyst layer on the electrode surface.

In summary, at any given instance using the exemplary embodiment above, there will always be 20 tips ready for testing 20 samples simultaneously. Each test takes 30 seconds to complete in this testing zone. Hence, this proposed carousel should be able to test 40 samples in a minute (or 2400 samples in an hour). Much like the single probe approach, electronics will be integrated to facilitate data storage on cloud and results can be obtained via a mobile app (FIG. 2B). The intended use for this multiprobe carousel is at frontlines including but not limited to hospitals, clinical laboratories, airports, schools, events, and universities, and other public places.

The hardware utilized to collect and display the testing results can include, for example, computers, intellectual property (IP) cores, application-specific integrated circuits (ASICs), programmable logic arrays, optical processors, programmable logic controllers, microcode, microcontrollers, servers, microprocessors, digital signal processors, or any other suitable circuit. Process may encompass any of the foregoing hardware, either singly or in combination. The hardware may comprise memory that may comprise a single disk or a plurality of disks (e.g., hard drives), and includes a storage management module that manages one or more partitions within the memory. In some embodiments, the memory may include flash memory, semiconductor (solid state) memory or the like. The memory may include Random Access Memory (RAM), a Read-Only Memory (ROM), or a combination thereof.

Figure 3B:
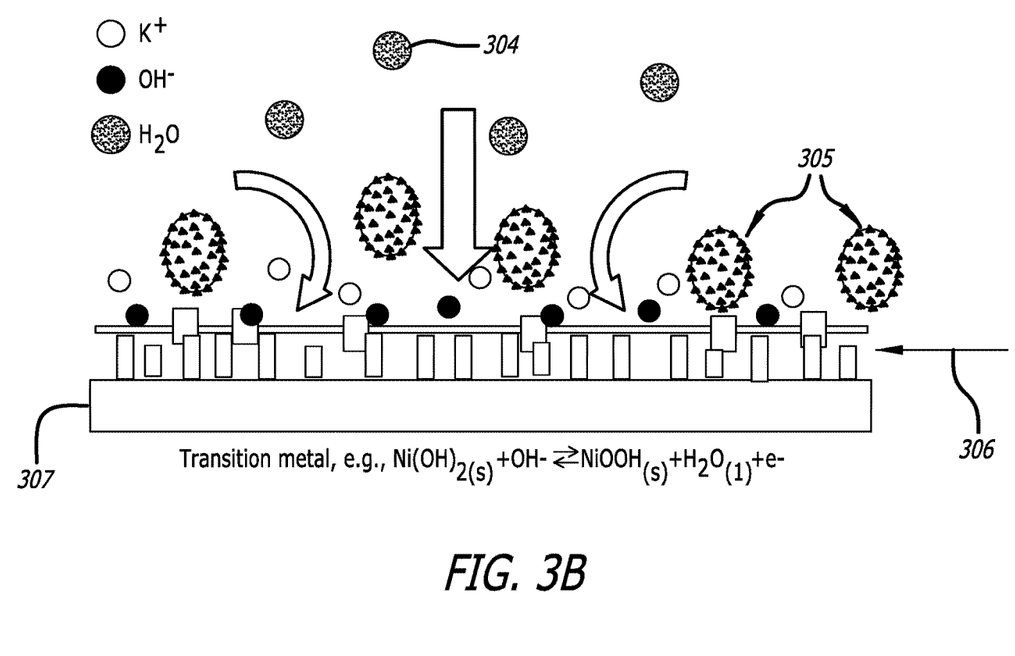
FIG. 3B depicts a schematic representation of the sensing mechanism for indication of the presence of a virus.

In some embodiments, the hardware associated with the sensor of the present invention may comprise an electronic device, such as a mobile app, via a network, as shown in FIG. 3B. The processors may be configured to communicate with the electronic device by uploading data into a cloud or other networked server. The processor may electrically communicate with the electronic device to facilitate communication between the sensor and the electronic device. It is to be appreciated the electronic device may be a computer, personal electronic device such as tablet, phone, watch, or any other electronic device (portable or non-portable, and including future electronic device). In some embodiments, the mobile app may be downloaded to the electronic device to facilitate communication between the sensor and the electronic device for interpreting the results obtained from the sensor. In some embodiments the mobile app includes a user interface for presenting information and receiving input or feedback from a user of the mobile app.

For the present invention, including as set forth in the claims, the term "processor" should be understood as encompassing any of the foregoing hardware, either singly or in combination. The terms "signal" and "data" are used interchangeably.

As used herein, the term module can include a packaged functional hardware unit designed for use with other components, a set of instructions executable by a controller (e.g., a processor executing software or firmware), processing circuitry configured to perform a particular function, and a self-contained hardware or software component that interfaces with a larger system. For example, a module can include an application specific integrated circuit (ASIC), a Field Programmable Gate Array (FPGA), a circuit, digital logic circuit, an analog circuit, a combination of discrete circuits, gates, and other types of hardware or combination thereof. In other embodiments, a module can include memory that stores instructions executable by a controller to implement a feature of the module.

Further, in one aspect, for example, systems described herein can be implemented using a general-purpose computer or general-purpose processor with a computer program that, when executed, carries out any of the respective methods, algorithms, and/or instructions described herein. In addition, or alternatively, for example, a special purpose computer/processor can be utilized which can contain other hardware for carrying out any of the methods, algorithms, or instructions described herein, including an electronic device as described herein.

Figure 6:
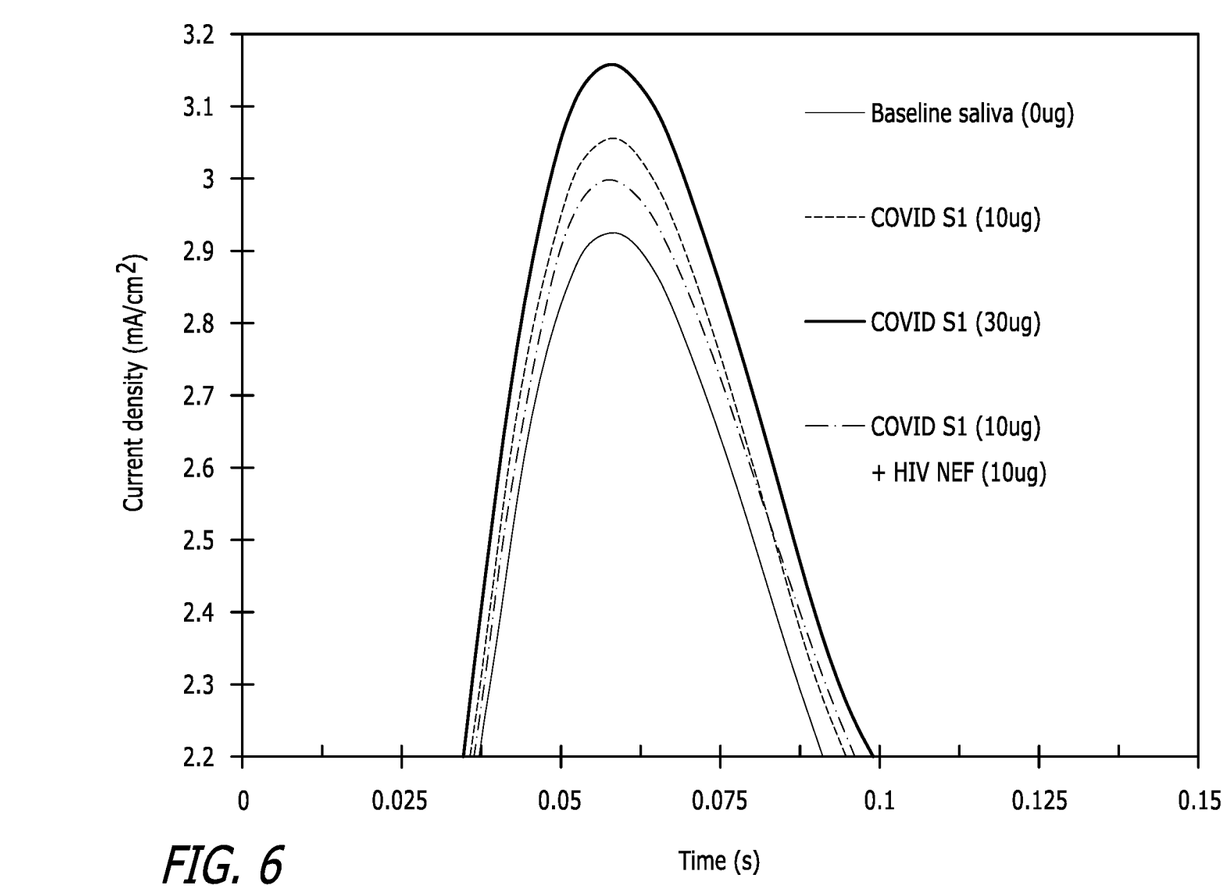
FIG. 6 depicts current responses recorded as a function of time from artificial saliva without any proteins (Baseline saliva), with 10 µg S1 protein, 10 µg S1 protein, and solution mixed with 10 µg S1 protein and 10 µg NEF protein, in accordance with at least some embodiments.

Rather than testing the SARS-CoV-2 proteins in phosphate buffer saline (PBS), an approach was made to test samples in a close-to-reality scenario wherein the sample collection was non-invasive (extends the applicability of the sensor as sample collection is easier). There are reports in the literature that up to 91.7% (11 out of 12) patients host detectable virus in saliva. Hence, for an exemplary embodiment a sample collection was a like field scenario where protein concentration of interest was mixed to 3 mL of medical-grade artificial saliva mixed with PBS and 1N potassium hydroxide solution (KOH) (commercial standardized solution) in a final volume of 20 mL to achieve a pH of 12. At such high pH, it is expected that cells and viruses will lyse and release proteins in solution. Therefore, present example benefited from the use of recombinant viral proteins. For this exemplary embodiment, two different concentrations of protein 51 of SARS-CoV-2 were tested in artificial saliva solution and the results are shown in FIG. 6. A clear distinction in current between the baseline (no protein) curve, and 10 μg and 30 μg of protein can be observed, meaning the protein in the solution has been detected. Even between the two different concentrations, there is a clear separation concluding the sensor of the present invention can be used to quantitatively detect coronavirus in saliva samples.

Figure 4:
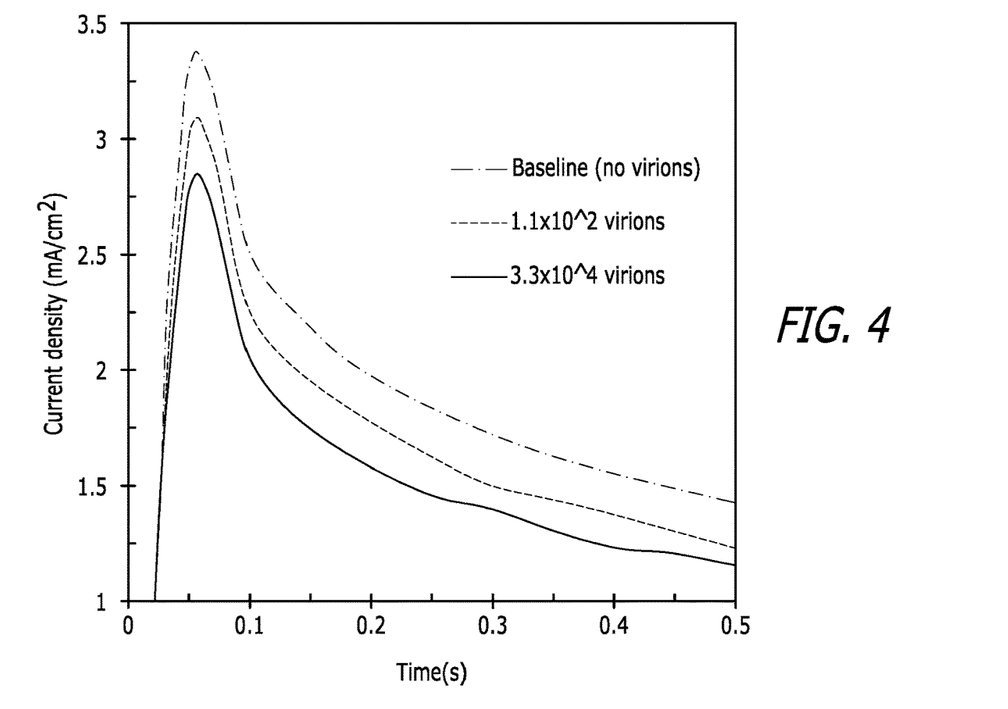
FIG. 4 depicts a chronoamperometry plot showing the difference in current between baseline and different concentrations of HIV virions, in accordance with at least some embodiments.

In one exemplary embodiment, a single probe sensor containing a sensor tip as shown in FIG. 1 with nickel working electrode and platinum counter and reference electrodes was coupled with a rotating disk electrode (Pine Instrument Company). These electrodes were dipped in 1M Potassium hydroxide (KOH) solution in water (Acros Organics' CAS #1310-58-3,7732-18-5) and the electrocatalyst was created locally on the sensor tip by running cyclic voltammetry (CV) in potential window of 0.2 to 0.6V vs. Pt reference electrode. Once this catalyst was formed, the sensor was immersed in a 20 ml solution containing phosphate buffer solution (PBS) and KOH to obtain the background current in the absence of HIV virions. Chronoamperometry test was performed at a rotation speed of 1600 rpm by oxidizing the electrode at 0.58V vs. Pt followed by reduction at 0.1V vs. Pt to retrieve the original nickel surface. Following this, the electrocatalyst was created again by performing CV and subsequently used for testing a 20 ml solution of PBS, the virions to be detected, and KOH for adjusting the pH. The resulting current responses from background and HIV virion solutions were recorded and the plotted results showing the current separation between the background and different virion concentrations are shown in FIG. 4.

Figure 5:
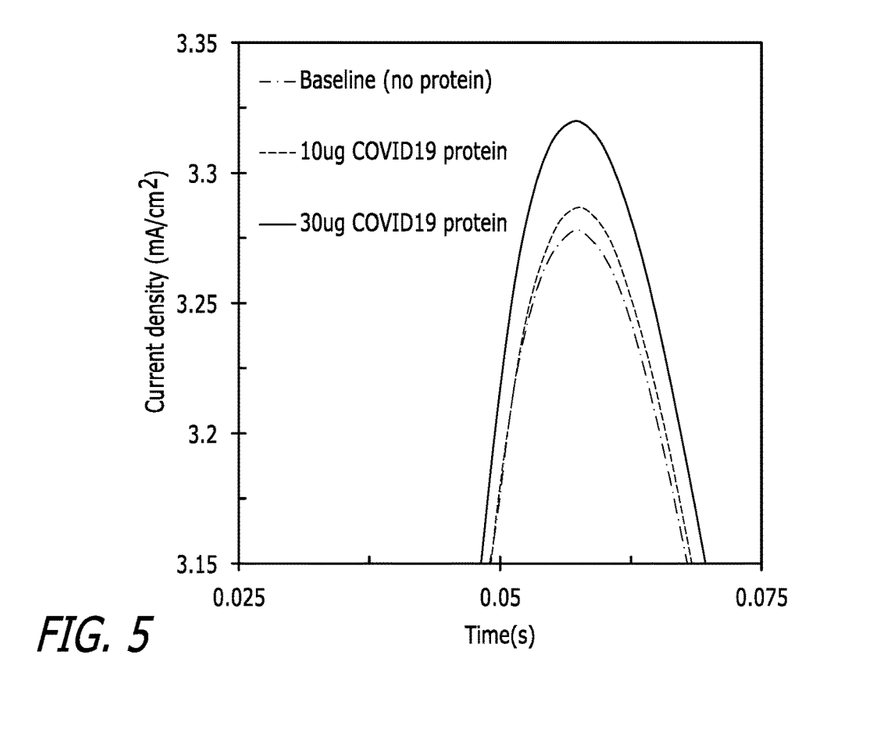
FIG. 5 depicts a chronoamperometry plot showing the difference in current between baseline and different concentrations of COVID-19 proteins.

In another exemplary embodiment, the sensor of the present invention was used for testing the spike proteins of virus causing COVID-19. The spike proteins were purchased from Ray Biotech (Recombinant SARS-CoV-2, 51 Subunit Protein, Code: 230-30162-100). The electrodes were immersed in KOH to form the electrocatalyst using the procedure for HIV virions. This electrocatalyst is used for obtaining the current response from background solution in the absence of COVID-19 proteins. Once the electrocatalyst was formed again by CV, the sensor tip was used for testing COVID-19 proteins of two different concentrations. The results from this exemplary embodiment (FIG. 5) revealed that the tested concentrations of COVID-19 proteins were distinguished by the sensor. The currents from COVID-19 protein are higher than the baseline current as compared to currents from HIV virions that have currents lower than baseline. This indicates the distinguishing factor for responses obtained from HIV virions as compared to COVID-19 proteins.

To further probe the specificity of RAnCODS-19 in capturing signals from SARS-CoV-2, a mixed solution containing equal quantities (10 μg each) of SARS-CoV-2 protein and Human Immunodeficiency Virus (HIV) NEF protein was prepared and tested. The reason for choosing HIV was because both HIV and SARS-CoV-2 are enveloped viruses in which glycoproteins are required for viral binding and penetration of their nucleic acid material into susceptible host cells. Although HIV is not a respiratory virus, both HIV and SARS-CoV are pandemic viruses with similar underlying disease-causing mechanisms, including severe T cell cytopathic effects. The response in currents of the mixed solution was compared to the responses in current from same concentration (10 μg) of these individual proteins. The results of this comparison are also depicted in FIG. 6. It is evident that the solution containing mix of NEF and gS1 proteins displayed responses more like the SARS-CoV-2 S1 protein alone. These responses even overlap around 75 ms showing that the S1 protein in mixed solution dominates and produces a current response almost similar as the response from 10 μg S1 protein only, thereby rendering specific detection of S1 protein over NEF protein.

Figure 7:
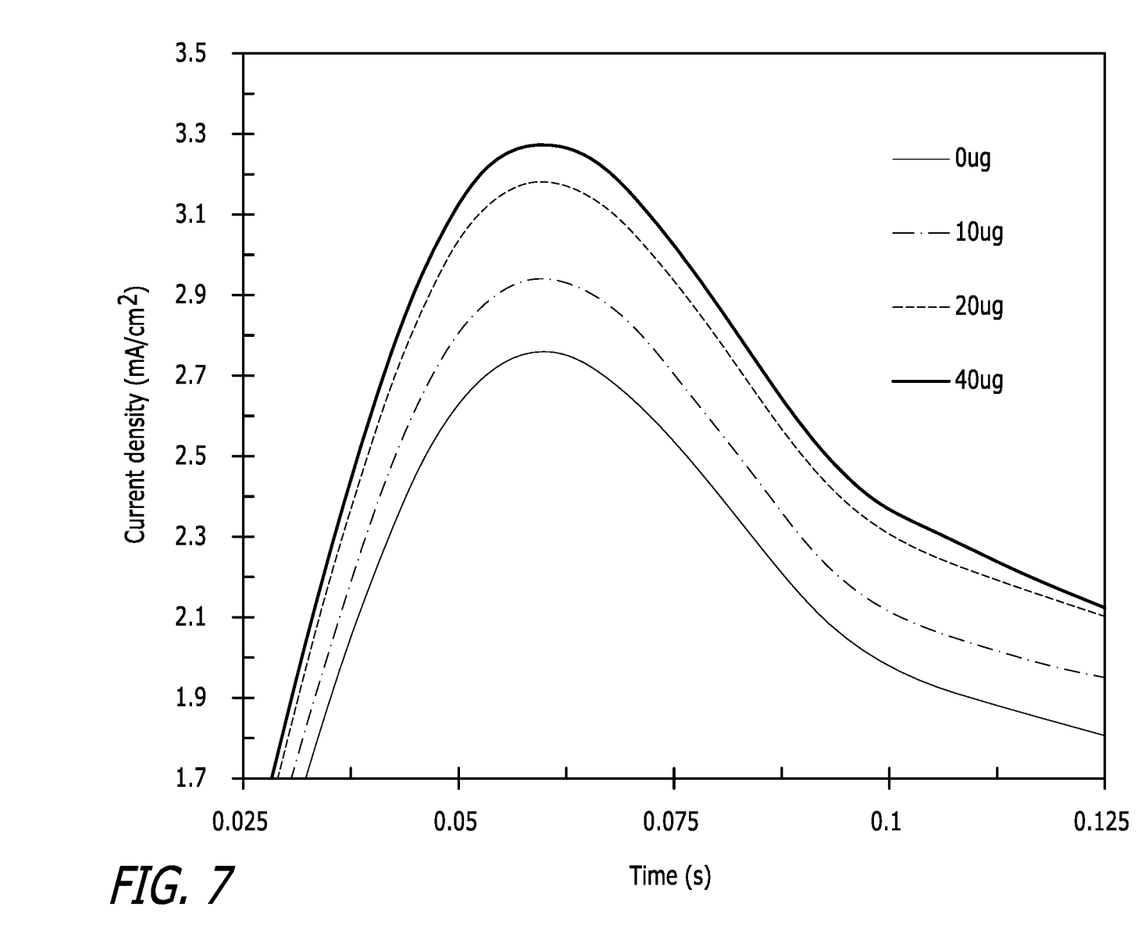
FIG. 7 depicts a chronoamperometry plot showing the current response of different concentrations of SARS-CoV-2 spike protein as a function of time, in accordance with at least some embodiments.

As an extension of the results of the previous examples, concentrations in the range of 10-40 μg diluted to 20 mL (0.5 to 2 μg/mL) were tested using the RAnCODS-19 device of the present invention. The current responses increased with increase in protein concentration as seen in FIG. 7. Using the current density values at 50 ms time point, a calibration curve was plotted equating the current response as a function of concentration of SARS-CoV-2 spike protein. Least squares linear regression was used to fit the data points ($R^2=0.89$). The approach consisted of using viral protein concentrations that were unknown to the engineer who analyzed the data in a blind fashion. The obtained calibration equation was used for predicting the concentration of a sample. The calibration plot obtained by plotting the current density value at 50 ms for different protein concentrations tested (blue points). The white outlined point corresponds to the concentration of sample solution predicted using the calibration equation:

$$i\left(\frac{mA}{cm^2}\right) = 0.2478c\left(\frac{mA}{cm^2}\right) + 2.6819\left(\frac{mA}{cm^2}\right).$$

Figure 8:
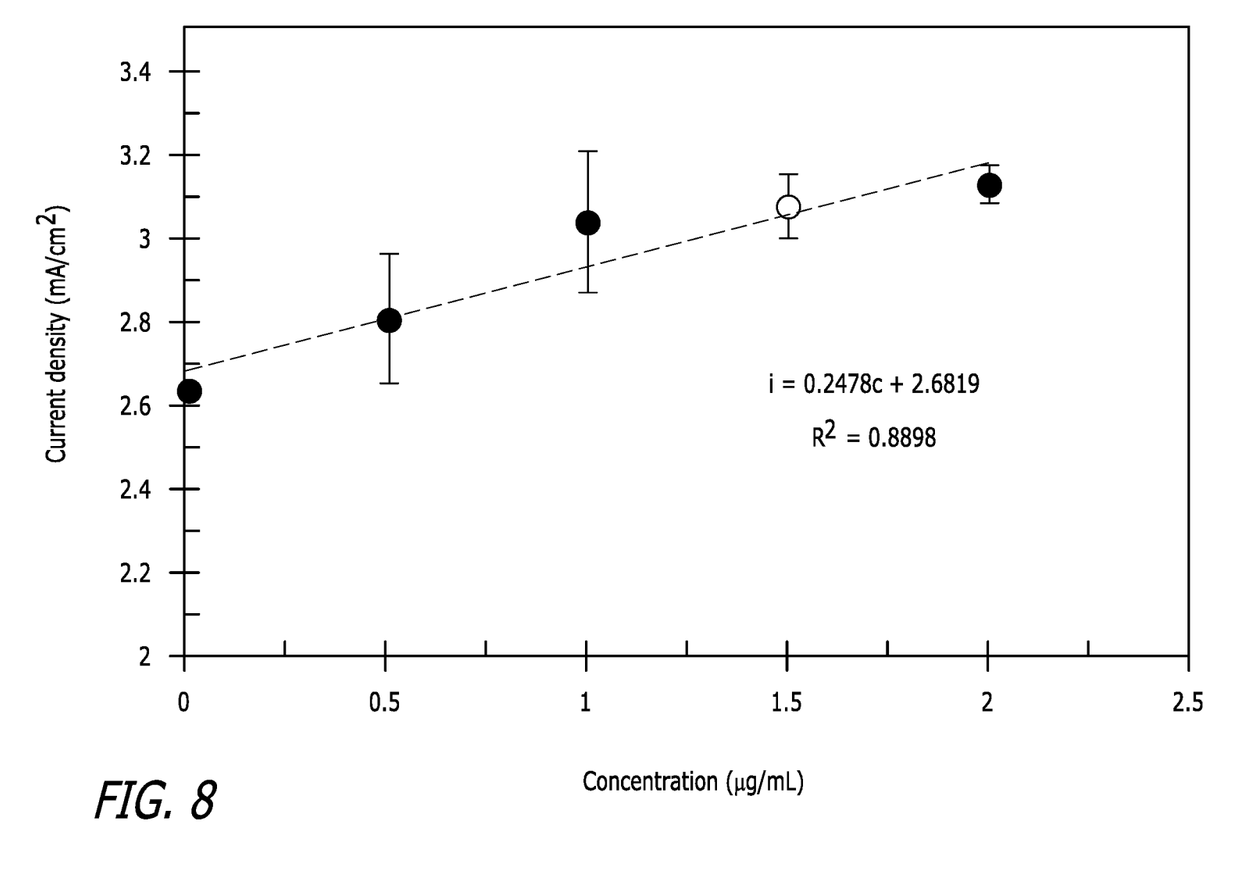
FIG. 8 depicts a calibration plot obtained by plotting the current density value at 50 ms, in accordance with at least some embodiments.

The current density value recorded for the unknown sample at 50 ms was substituted in the calibration equation in order to obtain the concentration of the sample FIG. 8. The actual concentration of the sample was 1.5 μg/mL (30 μg) and the concentration predicted by RAnCODS-19 prototype was 1.59 μg/mL (31.8 μg) with only 6% error compared to the actual concentration. Based on the slope of the calibration curve, the sensitivity of the sensor is 0.25 (mA/cm²)/(μg/mL). The limit of detection is given as LoD=3.3*($SD_{blank}$)/slope and the corresponding value for our case is found to be 0.04 μg/mL (0.8 μg/20 mL).

It is therefore that RAnCODS-19 represents a transformational innovation to pandemic diagnostics, the testing results are a reliable alternative to widely screening approaches like temperature checks and antibody test for the following reasons: 1) this device tests the presence of the actual virus directly, not the immune response; 2) the immune responses leading to antibody titers take time for the body to mount it, like the onset of fever. In both cases, asymptomatic patients can be easily missed, but not with the RAnCODS-19, as positive cases can be quarantined right away while awaiting for the molecular diagnosis; 3) The patients undergoing testing will not have to wait for hours or days to know the results; and 4) the epidemiological databases at the applicable Departments of Health can be updated almost instantly.

In another embodiment the RAnCODS-19 device of the present invention utilizes a potentiostat for applying voltage and recording current response, but this function may alternatively use a simple electronic circuit instead of the potentiostat, thereby making the device even more portable for point-of-care use with reduced capital cost. In addition to this, the data obtained from the RAnCODS-19 device can be stored in a cloud-based source to be processed and made available for viewing the results via a mobile app.

It is an additional embodiment that the present invention further brings significant relief in biosafety concerns related to SARS-CoV-2 research and clinical management, along with extra personal protective equipment (PPE) usage. All the measurements are carried out at pH 12, which is not compatible with physiological conditions needed for a virus to survive. Therefore, the testing conditions essentially destroy potentially infectious samples instantly, rendering any solutions non-infectious upon contact with the solution.

The operation cost (price/test) is low for the sensor of the present invention owing to the following factors: 1) the sensor tip is disinfected between experiments and reused, 2) the detection is rapid, hence the need for storing samples is no more required, and can be continually used for sample testing 3) no special equipment (like swabs or syringes) is required for sample collection since saliva is being used.

Example 1

Testing Procedure Using Sensor Probe

This example, describes a testing procedure that can be utilized with the sensor probe to detect a virus in a sample, in accordance with the invention.

In some embodiments, recombinant proteins can be safely handled under BSL1-2 conditions. For this example, the RAnCODS-19 prototype was handled under BSL2+ environments, inside a biosafety cabinet. The standard operating procedure for each sample consisted of three steps namely cyclic voltammetry (activation), chronoamperometry (testing), and rinsing step. The electrochemical measurements were performed using a Gamry Framework software associated with Gamry Reference 600+ Potentiostat.

In the example, the first step included cyclic voltammetry. In this embodiment, the cyclic voltammetry (CV) experiments were performed using a nickel working electrode (5 mm diameter) inserted in a rotating disk electrode setup (Pine Instrument Company MSRX Speed Control Analytical Rotator), platinum ring counter electrode (ESPI metals, 0.75"×0.2"×0.005") placed concentric to working electrode and a platinum foil (ESPI metals, 0.3"×0.1"×0.005") used as pseudo reference electrode. Further, in this embodiment, the electrolyte was 20 mL of commercially purchased 1N KOH solution. The CVs were performed in a potential window of 0.20 to 0.60 V and scan rate of 15 mV/s for 5 cycles, with the fifth cycle being the sustained periodic cycle.

In Example 1, following the CV curve generation, the step of chronoamperometry was begun. For this step in Example 1, the sample for testing was prepared by adding the desired amount of protein or saliva and diluting it to 19.3 mL using PBS solution. A solution of 0.7 mL 1N KOH was added to this solution to bring the pH to 12. In these embodiments, chronoamperometry experiments were performed at pH 12 and 1600 rpm. This 20 mL of as-prepared solution was the test solution used. Specifically, chronoamperometry was performed by recording the open circuit potential for 60 seconds followed by a fixed oxidation potential of 0.58 V vs. Pt for 5 seconds and a fixed reduction potential of 0.10 V vs. Pt for 15 seconds.

For the example, following the draining of the test solution, fresh 1N KOH solution was pumped in and held idle for 30 seconds to disinfect the chamber. This process was repeated twice before moving to the activation for subsequent test.

In the embodiment, the experiment continued with the data analysis of Example 1. The data obtained from Gamry Framework software were imported to Microsoft Excel (2016 version) for data analysis. The error bars presented in the plots include the positive and negative deviations from the average currents of triplicate measurements.

Additionally, in this Example 1, Human saliva samples were obtained from consenting individuals who did not have any history of SARS-CoV-2 infection. The samples were triple-blinded to mask the identity of the donors.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

REFERENCES

1. Xu, S. & Li, Y. Beware of the second wave of COVID-19. *The Lancet* 395, 1321-1322 (2020).
2. D'Arienzo, M. & Coniglio, A. Assessment of the SARS-CoV-2 basic reproduction number, R0, based on the early phase of COVID-19 outbreak in Italy. *Biosafety and Health* S2590053620300410 (2020) doi:10.1016/j.bshea1.2020.03.004.
3. Li, Q. et al. Early Transmission Dynamics in Wuhan, China, of Novel Coronavirus-Infected Pneumonia. *N Engl J Med* 382, 1199-1207 (2020).
4. Li, R. et al. Substantial undocumented infection facilitates the rapid dissemination of novel coronavirus (SARS-CoV-2). *Science* 368, 489-493 (2020).
5. Wang, D. et al. Clinical Characteristics of 138 Hospitalized Patients With 2019 Novel Coronavirus-Infected Pneumonia in Wuhan, China. *JAMA* 323, 1061 (2020).
6. Tang, Y.-W., Schmitz, J. E., Persing, D. H. & Stratton, C. W. Laboratory Diagnosis of COVID-19: Current Issues and Challenges. *J Clin Microbiol* 58, e00512-20, /jcm/58/6/JCM.00512-20.atom (2020).
7. Dheda, K. et al. Diagnosis of COVID-19: Considerations, Controversies and Challenges in South Africa. *WJCM* 2, 3 (2020).
8. Yang, S. & Rothman, R. E. PCR-based diagnostics for infectious diseases: uses, limitations, and future applications in acute-care settings. *The Lancet Infectious Diseases* 4, 337-348 (2004).
9. Gutierres, S. L. & Welty, T. E. Point-of-Care Testing: An Introduction. *Ann Pharmacother* 38, 119-125 (2004).
10. Gandhi, M., Yokoe, D. S. & Havlir, D. V. Asymptomatic Transmission, the Achilles' Heel of Current Strategies to Control Covid-19. *N Engl J Med* 382, 2158-2160 (2020).

11. Wang, W. et al. Detection of SARS-CoV-2 in Different Types of Clinical Specimens. *JAMA* (2020) doi:10.1001/jama.2020.3786.
12. Zou, L. et al. SARS-CoV-2 Viral Load in Upper Respiratory Specimens of Infected Patients. *N Engl J Med* 382, 1177-1179 (2020).
13. Kim, C. et al. Comparison of Nasopharyngeal and Oropharyngeal Swabs for the Diagnosis of Eight Respiratory Viruses by Real-Time Reverse Transcription-PCR Assays. *PLoS ONE* 6, e21610 (2011).
14. Blaschke, A. J. et al. Non-invasive sample collection for respiratory virus testing by multiplex PCR. *Journal of Clinical Virology* 52, 210-214 (2011).
15. Bilder, L., Machtei, E. E., Shenhar, Y., Kra-Oz, Z. & Basis, F. Salivary Detection of H1N1 Virus: A Clinical Feasibility Investigation. *J Dent Res* 90, 1136-1139 (2011).
16. Pasomsub, E. et al. Saliva sample as a non-invasive specimen for the diagnosis of coronavirus disease 2019: a cross-sectional study. *Clinical Microbiology and Infection* S1198743X20302780 (2020) doi:10.1016/j.cmi.2020.05.001.
17. Sindhu, S. & Jagannathan, N. Saliva: A Cutting Edge in Diagnostic Procedures. *Journal of Oral Diseases* 2014, 1-8 (2014).
18. Azzi, L. et al. Saliva is a reliable tool to detect SARS-CoV-2. *Journal of Infection* 81, e45-e50 (2020).
19. To, K. K.-W. et al. Consistent Detection of 2019 Novel Coronavirus in Saliva. *Clinical Infectious Diseases* ciaa149 (2020) doi:10.1093/cid/ciaa149.
20. Williams, E., Bond, K., Zhang, B., Putland, M. & Williamson, D. A. Saliva as a non-invasive specimen for detection of SARS-CoV-2. *J Clin Microbiol* JCM.00776-20, jcm; JCM.00776-20v1 (2020) doi:10.1128/JCM.00776-20.
21. Vedharathinam, V. & Botte, G. G. Understanding the electro-catalytic oxidation mechanism of urea on nickel electrodes in alkaline medium. *Electrochimica Acta* 81, 292-300 (2012).
22. Seo, G. et al. Rapid Detection of COVID-19 Causative Virus (SARS-CoV-2) in Human Nasopharyngeal Swab Specimens Using Field-Effect Transistor-Based Biosensor. *ACS Nano* 14, 5135-5142 (2020).
23. Thévenot, D. R., Toth, K., Durst, R. A. & Wilson, G. S. ELECTROCHEMICAL BIO SENSORS: RECOMMENDED DEFINITIONS AND CLASSIFICATION *. *Analytical Letters* 34, 635-659 (2001).
24. Kliger, Y. & Levanon, E. Y. Cloaked similarity between HIV-1 and SARS-CoV suggests an anti-SARS strategy. *BMC Microbiology* 7 (2003).
25. Khodamoradi, Z., Moghadami, M. & Lotfi, M. Co-infection of Coronavirus Disease 2019 and Influenza A: A Report from Iran. *Arch Iran Med* 23, 239-243 (2020).
26. Kim, D., Quinn, J., Pinsky, B., Shah, N. H. & Brown, I. Rates of Co-infection Between SARS-CoV-2 and Other Respiratory Pathogens. *JAMA* 323, 2085 (2020).
27. Konala, V. M. et al. Co-infection with Influenza A and COVID-19. *European Journal of Case Reports in Internal Medicine* 7, 1 (2020).
28. Altuntas Aydin, O., Kumbasar Karaosmanoglu, H. & Kart Yasar, K. HIV/SARS-CoV-2 coinfected patients in Istanbul, Turkey. *J Med Virol* jmv.25955 (2020) doi: 10.1002/jmv.25955.
29. Zhu, F., Cao, Y., Xu, S. & Zhou, M. Co-infection of SARS-CoV-2 and HIV in a patient in Wuhan city, China. *J Med Virol* 92, 529-530 (2020).
30. Parker, A. et al. HIV and SARS-CoV-2 co-infection: The diagnostic challenges of dual pandemics. *S Afr Med J* 110, (2020).
31. Wang, W.-K. et al. Detection of SARS-associated Coronavirus in Throat Wash and Saliva in Early Diagnosis. *Emerg. Infect. Dis.* 10, 1213-1219 (2004).
32. Liu, L. et al. Epithelial Cells Lining Salivary Gland Ducts Are Early Target Cells of Severe Acute Respiratory Syndrome Coronavirus Infection in the Upper Respiratory Tracts of Rhesus Macaques. *Journal of Virology* 85, 4025-4030 (2011).
33. Xu, J., Li, Y., Gan, F., Du, Y. & Yao, Y. Salivary Glands: Potential Reservoirs for COVID-19 Asymptomatic Infection. *J Dent Res* 002203452091851 (2020) doi:10.1177/0022034520918518.
34. Sabino-Silva, R., Jardim, A. C. G. & Siqueira, W. L. Coronavirus COVID-19 impacts to dentistry and potential salivary diagnosis. *Clin Oral Invest* 24, 1619-1621 (2020).
35. Humphrey, S. P. & Williamson, R. T. A review of saliva: Normal composition, flow, and function. *The Journal of Prosthetic Dentistry* 85, 162-169 (2001).
36. Lopin, P. & Lopin, K. V. PSoC-Stat: A single chip open source potentiostat based on a Programmable System on a Chip. *PLoS ONE* 13, e0201353 (2018).
37. Ramanujam and Botte. Online Sensor Device for Rapid *Escherichia coli* Detection in Water. In *ECS Meeting Abstracts;* 2018.
38. Jiang et al. COVID-19 Diagnostics: Technologies, Players and Trends. IDTechEx. (accessed Jun. 19, 2020).

The invention claimed is:
1. A sensor for detecting a virus with a sensor tip comprising:
 (a) a working electrode, wherein the working electrode comprises
  (i) a conductive material, wherein the conductive material is resistant to corrosion,
  (ii) a support, and
  (iii) a catalyst;
 (b) a counter electrode comprising an electrocatalyst, wherein
  (i) the counter electrode is operably connected to the working electrode,
  (ii) the sensor tip when inserted into a media is operable for detecting change in current utilizing the working electrode and the counter electrode, and
  (iii) the sensor tip is operable for detecting the virus by the change in current when inserted into the media comprising a composition that comprises a sample and pH adjusting salts, wherein the sample is selected from a group consisting of Saliva, Plasma, Phosphate buffered saline (PBS), Dulbecco's Phosphate buffered saline (DPBS), and combinations thereof.
2. The sensor of claim 1 further comprising a reference electrode comprising a reference material.
3. The sensor of claim 2, wherein the reference material is selected from a group consisting of Pt, Au, Ag, Ti, Rh, Ru, and combinations thereof.
4. The sensor of claim 2, wherein the sensor tip when inserted into the media is operable for detecting change in current utilizing the reference material in combination with the working electrode and the counter electrode.
5. The sensor of claim 1, wherein the support is selected from a group consisting of Nickel, Nickel gauze, Nickel mesh, Ti, stainless steel, Hastelloy, graphite, nickel foam, Ti foam, Aluminum, Aluminum foam, carbon, carbon fibers, and graphene.

6. The sensor of claim 1, wherein the catalyst comprises a transition metal.

7. The sensor of claim 6, wherein the transition metal is selected from a group consisting of Ni, Fe, Co, Cr, Mo, Rh, Ru, Pd, Ir, Au, Pt, composites of graphene metal, and combinations thereof.

8. The sensor of claim 6, wherein the transition metal comprises Ni.

9. The sensor of claim 1, wherein the support comprises the catalyst.

10. The sensor of claim 1, wherein the electrocatalyst is selected from a group consisting of Pt, Au, Ir, Ni, Ti, Rh, Ru, and combinations thereof.

11. The sensor of claim 1, wherein the virus being detected is selected from a group consisting of coronavirus (SARS-CoV-2), Human Immunodeficiency Virus (HIV), pandemic viruses, and combinations thereof.

12. The sensor of claim 1, wherein the sensor is operable for detecting the virus within a time period in the range between 10 milliseconds and 10 seconds.

13. The sensor of claim 12, wherein the sensor is operable for detecting concentration of a second virus in the sample.

14. The sensor of claim 1, wherein the sensor is operable for detecting the virus within 100 milliseconds.

15. The sensor of claim 1, wherein the sensor is operable for detecting concentration of the virus in a sample.

16. A method for detecting a virus with a sensor tip, the method comprising:
  (a) selecting a sensor tip, wherein the sensor tip comprises
    (i) a working electrode, wherein the working electrode comprises a conductive material,
    (ii) a counter electrode, wherein the counter electrode comprises an electrocatalyst, and
    (iii) a reference electrode, wherein the working electrode is operably connected to the counter electrode and the reference electrode;
  (b) creating a catalyst locally on the sensor tip, wherein
    (i) the catalyst is created at a particular voltage, and
    (ii) the particular voltage corresponds to the working electrode and the reference electrode;
  (c) inserting the sensor tip into a media comprising a composition that comprises a sample and pH adjusting salts, wherein the sample is selected from a group consisting of Saliva, Plasma, Phosphate buffered saline (PBS), Dulbecco's Phosphate buffered saline (DPBS), and combinations thereof;
  (d) rotating the sensor tip, wherein the sensor tip is rotated at a particular rotation speed;
  (e) applying a cell voltage between the working electrode and the reference electrode;
  (f) holding the sensor tip at a particular temperature;
  (g) calibrating a change in current between a media blank and the media; wherein
    (i) the media blank comprises a virus-free sample, and
    (ii) the change in current is calibrated as a function of concentration of the virus present in the media.

17. The method of claim 16, wherein the virus being detected is selected from a group consisting of coronavirus (SARS-CoV-2), Human Immunodeficiency Virus (HIV), pandemic viruses, and combinations thereof.

18. The method of claim 16, wherein the sensor is operable for detecting the virus within 10 seconds.

19. The method of claim 16, wherein the sensor is operable for detecting the virus within 100 milliseconds.

20. The method of claim 16, wherein the media that the sensor tip is inserted into comprises a single sample.

21. The method of claim 16, wherein the media that the sensor is inserted into comprises multiple samples.

22. The method of claim 21, wherein the multiple samples enable calibrating multiple probes simultaneously.

23. The method of claim 16, wherein the pH adjusting salts are selected from a group consisting of KOH, NaOH, ammonium solutions, phosphate buffers, and combinations thereof.

24. The method of claim 16, wherein the particular rotation speed is in a range between 0 rpm and 3000 rpm.

25. The method of claim 16, wherein the cell voltage is in a range between −0.5 V and 1.0 V relative to voltage of the reference electrode.

26. The method of claim 16, wherein the particular temperature is in a range between 10° C. and 40° C.

27. The method of claim 16, wherein the sensor is operable for detecting concentration of a second virus in the sample.

* * * * *